United States Patent [19] [11] 4,208,786
Merchant et al. [45] Jun. 24, 1980

[54] TITANIA THERMISTOR AND METHOD OF FABRICATING

[75] Inventors: Stanley R. Merchant, Garden City; Michael J. Cermak, Southfield, both of Mich.

[73] Assignee: Ford Motor Company, Dearborn, Mich.

[21] Appl. No.: 963,614

[22] Filed: Nov. 24, 1978

Related U.S. Application Data

[62] Division of Ser. No. 839,700, Oct. 5, 1977, abandoned.

[51] Int. Cl.² ........................... H01C 7/00; G01N 7/02
[52] U.S. Cl. ........................................ 29/612; 29/621; 73/27 R; 338/14; 338/22 SD; 338/23
[58] Field of Search ............. 29/612, 610, 611, 613, 29/621; 73/27 R, 23; 338/14, 22 SD, 23, 24, 25, 28, 229; 422/96

[56] References Cited

U.S. PATENT DOCUMENTS

| 3,186,835 | 6/1965 | Bundy | 338/22 SD |
| 3,639,132 | 2/1972 | Egerton | 264/332 |
| 3,699,803 | 10/1972 | Sumi | 73/27 R |
| 3,886,785 | 6/1975 | Stadler | 73/23 |
| 4,007,435 | 2/1977 | Tien | 338/34 |
| 4,029,472 | 6/1977 | Micheli | 422/108 |

Primary Examiner—Francis S. Husar
Assistant Examiner—Gene P. Crosby
Attorney, Agent, or Firm—Robert W. Brown; Clifford L. Sadler

[57] ABSTRACT

A high temperature thermistor and its method of fabrication are disclosed. The thermistor is fabricated from titanium dioxide ceramic forming material and is fabricated to achieve a high degree of densification approaching 100% of theoretical density. At elevated temperatures in the range of from about 700° F. to about 1500° F. densified titania ceramic material behaves as a semiconductor having a resistance which is responsive principally to the temperature of the thermistor element. The thermistor is fabricated by processing titania powder which includes a substantial majority of rutile phase material. The titania powder is processed to achieve a thermistor chip or member which demonstrates a high degree of density.

4 Claims, 3 Drawing Figures

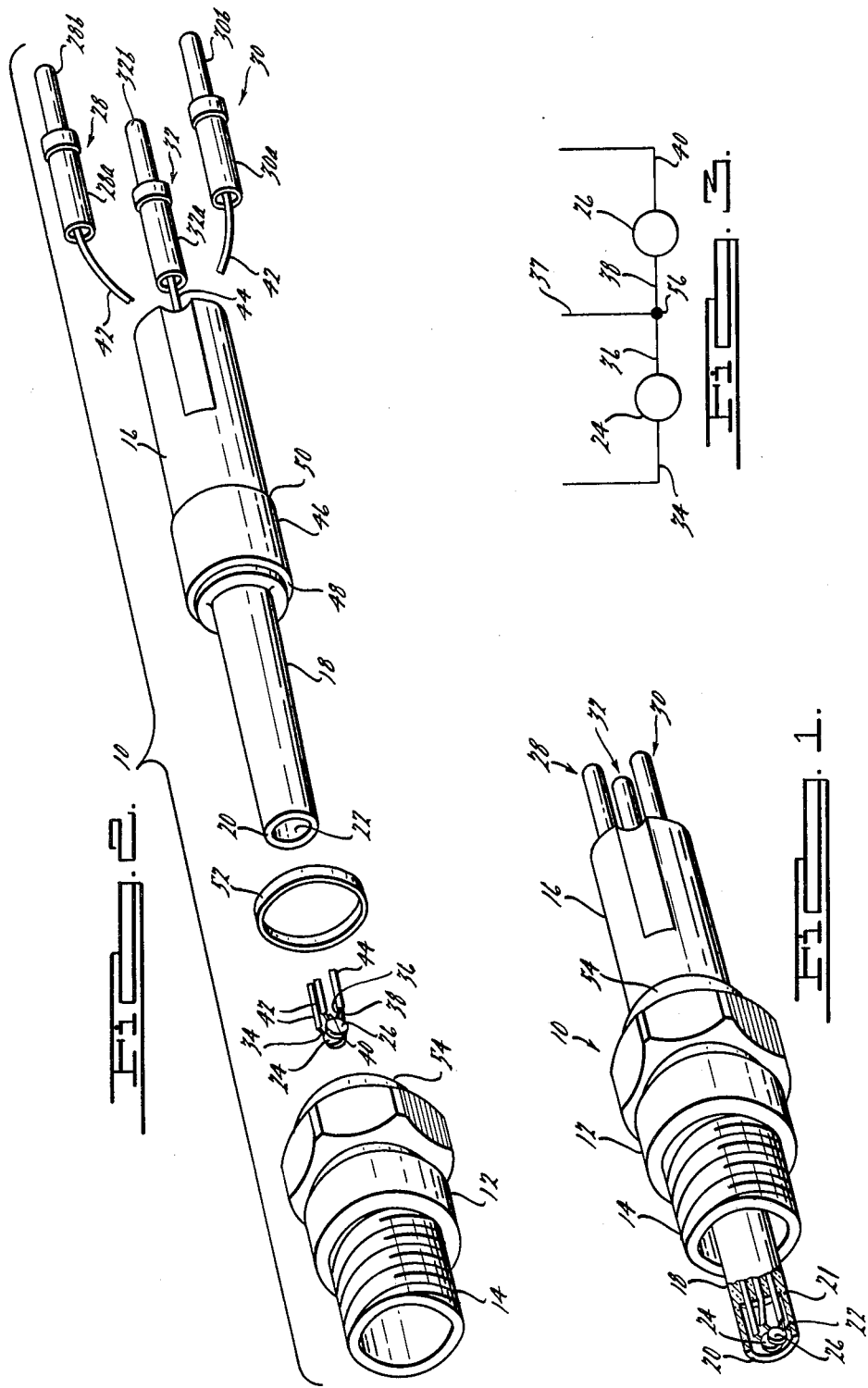

TITANIA THERMISTOR AND METHOD OF FABRICATING

This is a division of application Ser. No. 839,700, filed Oct. 5, 1977, now abandoned.

CROSS REFERENCE TO RELATED APPLICATION

This application is related to copending commonly filed patent application Ser. No. 839,704, now U.S. Pat. No. 4,151,503, issued Apr. 24, 1979, filed in the names of S. R. Merchant and M. J. Cermak and titled "Temperature Compensated Resistive Exhaust Gas Sensor Construction". This related application is assigned to the assignee of this application.

BACKGROUND OF THE INVENTION

1. Field of the Invention

The present invention is directed to the field of temperature responsive devices. More particularly still, the present invention is directed to that portion of the above-noted field which is concerned with the sensing of relatively high temperatures in the range of from about 700° F. to about 1500° F. More particularly still, the present invention is directed to that portion of the above-noted field which is concerned with generating an electrically measurable response to changes in sensed, relatively high, temperature. More particularly still, the present invention is directed to that portion of the above noted field which is concerned with the provision of ceramic semiconductive elements having an electrical parameter which varies predictably and repeatably in response to variation in a sensed temperature. More particularly still, the present invention is directed to that portion of the above-noted field which is concerned with the provision of a ceramic semiconductive element having a resistance which varies predictably and repeatably in response to variation in a sensed temperature. More particularly still, the present invention is directed to that portion of the above-noted field which is concerned with the provision of gas temperature sensing elements suitable for insertion within the exhaust system of a combustion source in order to monitor the temperature of the exhaust gas within the system.

2. Description of the Prior Art

It has been determined that the operation of a conventional automotive internal combustion engine produces substantially quantities of deleterious gaseous combustion by products. The principal pollutants so produced are hydrocarbons, carbon monoxide and varies oxides of nitrogen. Extensive investigation into the combustion process, examination of alternative combustion processes and detailed studies of exhaust gas treatment devices have led to the conclusion that the use of a catalytic converter within the exhaust system of an internal combustion engine provides a practical and effective technique for substantially reducing the emission of the deleterious gaseous combustion by products into the atmosphere.

A catalytic exhaust gas treatment device or converter which is capable of substantially simultaneously converting all three of the aforementioned principal pollutants into water, carbon dioxide and gaseous nitrogen is referred to as a "three-way catalyst". However, for the known three-way catalyst devices to be most effective, the gaseous by products introduced into the converter must be the by products of combustion of a substantially stoichiometric air/fuel ratio. Such three-way catalyst devices are said to have a very narrow "window" of air/fuel ratios at which the device is most efficiently operative on the three principal pollutants. By way of example, $\lambda$ is the air/fuel ratio normalized to stoichiometry, the window may extend from about $0.99\lambda$ to about $1.01\lambda$. Such a three-way catalyst device is described, for example, in U.S. Pat. No. 3,895,093 issued to Weidenbach et al. on July 15, 1975, assigned to Kali Chemie Aktiengesellschaft and titled "Catalytic Removal of Carbon Monoxide Unburned Hydrocarbon and Nitrogen Oxide from Automotive Exhaust Gas". For air/fuel ratios of the combustion mixture on either side of the window, one or two of the principal pollutants will be converted in only very small percentage efficiencies. Within the window, the three principal pollutants will be converted at very high efficiencies approaching 90% in some cases. In view of the narrowness of the catalytic converter window it has been determined that the associated internal combustion engine must be operated with a combustible mixture as close as possible to stoichiometry.

The most satisfactory technique for assuring continuous or substantially continuous operation at the optimum air/fuel ratio is through the utilization of an appropriate feedback mechanism. In implementing suitable feedback control systems it has been proposed to employ sensors responsive to the chemistry of the exhaust gases, that is, the hot gaseous combustion by-products, in order to control the precise air content and/or fuel content of the air/fuel mixture being provided to the engine. One type of electrochemical exhaust gas sensor employs a ceramic material which demonstrates a predictable electrical resistance change when the partial pressure of oxygen of its environment changes. An example of such a material is titania (titanium dioxide having a general formula $TiO_2$). Such sensors can be fabricated generally in accordance with the teachings of U.S. Pat. No. 3,886,785 issued to Stadler et al., titled "Gas Sensor and Method of Manufacture" and assigned to the assignee hereof. Tests of such devices have shown that at elevated and substantially constant temperatures the devices will demonstrate a virtual step change in resistance for richto-lean and lean-to-rich excursions of the air/fuel ratio of the combustion mixture producing the exhaust gas environment of the device.

A principal difficulty which has been encountered with such variable resistance devices resides in the fact that such devices will demonstrate a measurable resistance change which is also a function of change of the temperature of the ceramic material. For example, a temperature change of about 500° F. produces a measurable resistance change on the order of magnitude of a sensed rich-to-lean or lean-to-rich air/fuel mixture change. Such a temperature variation may be encountered, depending of course to some extent on the location of placement of the sensor within an exhaust system, during acceleration of the associated engine from idle speed to highway speeds. Heretofore, exhaust gas sensors which employed a variable resistance sensor ceramic have required that the temperature of the material be relatively closely controlled for reliable use in a feedback system intended to provide an internal combustion engine with very precise air/fuel ratio control.

Temperature control of the associated sensor has proved to be an expensive and not wholly satisfactory technique for adapting such variable resistance sensor ceramic materials to air/fuel ratio feedback control systems in automotive internal combustion engines. In order to overcome the difficulties encountered, it has been suggested to combine a thermistor in an electrical series circuit with the variable resistance exhaust gas sensor and to operate the electrical series circuit as a voltage divider network deriving a useful voltage signal from the junction between the thermistor and the variable resistive gas sensor element. However, known thermistors are temperature limited to such a degree that it is an object of the present invention to provide a thermistor capable of operating within the exhaust gas environment of an internal combustion engine. More particularly still, it is an object of the present invention to provide a semiconductive variably resistive ceramic element capable of withstanding temperatures in the range of from about 700° F. to about 1500° F. for extended periods of time and which is otherwise capable of tolerating the adverse environment of an automotive engine exhaust system. It is a further and specific object of the present invention to provide a sturdy, ceramic, high temperature thermistor which is electrically compatible with use as a portion of a voltage divider network having as the other portion thereof a variable resistive oxygen responsive ceramic member.

SUMMARY OF THE PRESENT INVENTION

In analyzing the reason why a partial pressure of oxygen responsive ceramic material such as titania also demonstrates a measurable resistance change in the presence of variation in temperature, it was determined that titania ceramic material functions as a composite variable resistor having a resistance variation component which is responsive to changes in partial pressure of oxygen and a further resistance component which is responsive to changes in temperature. Since the prior art teaches that the responsiveness of the oxygen sensitivity of titania ceramic material operated at high temperature is promoted in large measure by maintaining a porous device, we have determined that a suitable high temperature thermistor may be fabricated by utilizing titania ceramic material which is processed to achieve a density which closely approaches the theoretical density of the material. We have determined that substantial reductions in the oxygen sensitivity responsiveness of the titania material will produce a device which behaves as if it were not responsive to oxygen concentrations at all in the time frame of normal automotive vehicle operation. The present invention thus provides a thermistor comprised of titania ceramic material which has been processed to achieve a density approaching 100% of theoretical density for use in combination with a variable resistive partial pressure of oxygen responsive ceramic in an exhaust gas sensor as described in the cross referenced patent application.

DESCRIPTION OF THE DRAWING

FIG. 1 illustrates an exhaust gas sensor construction incorporating a thermistor according to the present invention.

FIG. 2 illustrates, in an exploded view, the exhaust gas sensor according to FIG. 1.

FIG. 3 illustrates the electrical series connection of the partial pressure of oxygen responsive ceramic sensor member with a thermistor member according to the present invention.

DETAILED DESCRIPTION OF THE PREFERRED EMBODIMENT

Referring now to the drawing wherein like numerals designate like structure throughout the various views thereof, an exhaust gas sensor 10 is shown in FIG. 1. Exhaust gas sensor 10 is of utility, for example, as the partial pressure of oxygen responsive element insertable into the exhaust system of an internal combustion engine or a furnace for monitoring the partial pressure of oxygen of the gaseous combustion by-products produced thereby in order to generate a signal indicative of the quality of the combustion process. In particular, the equivalence ratio, λ, of the combustion mixture being provided to the engine or furnace may be determined by analysis of the partial pressure of oxygen within the exhaust gases.

With reference now to FIGS. 1 and 2, and particularly to FIG. 2, the exhaust gas sensor 10 incorporating the present invention is illustrated and one possible method of assembly is described. Exhaust gas sensor 10 is provided with a housing means 12 which is threaded as at 14 for engagement with a suitably threaded aperture provided therefor within the exhaust gas conduit, not shown, of the combustion source. Ceramic insulator member 16 extends through housing means 12 and includes a forwardly projecting sensor support portion 18. Sensor support portion 18 includes forwardly projecting collar 20 which defines a well or cavity 22. Forwardly projecting portion 18 is broken away at 21 in FIG. 1 for illustrative purposes. The sensor 10 includes a pair of ceramic sensor elements or members 24, 26 received within well 22. Three electrical terminal members 28, 30, 32 extend rearwardly from ceramic insulator member 16. Electrical terminal members 28, 30, 32 are adapted for receipt of suitable mating connectors, not shown, to electrically communicate exhaust gas sensor 10 with associated utilization electrical or electronic circuitry, not shown.

The insert portions 28a, 30a, 32a of each of the electrical terminal members 28, 30, and 32 may be cemented into position within the rear portion of ceramic insulator member 16. The preferred cement is a catalytic agent, low temperature curable cement which cures to a high density. Such a cement may be, for example Sauereisen #31. The terminal members 28, 30 and 32 are arranged to project an electrical contact portion 28b, 30b and 32b of each terminal member 28, 30 and 32 rearwardly from the rear face of ceramic insulator member 16.

The ceramic sensor elements 24, 26 comprise a partial pressure of oxygen responsive ceramic such as titania, for example sensor element 26, and a temperature compensating thermistor according to the present invention, for example sensor element 24. As used herein the term thermistor refers to an electronic device which has an electrical parameter or property, such as its electrical resistance, which varies rapidly and predictably with the temperature of the device and which parameter or property varies only slightly, if at all, in short periods of time in response to changes in partial pressure of oxygen of the environment of the device.

The thermistor element according to the present invention, ceramic sensor element 24, is connected electrically in series with the partial pressure of oxygen responsive element, sensor element 26, in order to compensate for any tendency of the partial pressure of oxygen responsive element 26 to change its electrical parameter or property in response to temperature variation. The series connected ceramic sensor element 24, 26 are arranged to be exposed to substantially the same exhaust gas environment and are arranged to define an electrical voltage divider network wherein the desired output signal is derived from the circuit junction between the ceramic sensor elements, i.e., the junction of the thermistor element with the partial pressure of oxygen responsive sensor element.

Each ceramic sensor element 24, 26 is provided with a pair of electrical leads 34, 36, 38, 40. Electrical leads 34 and 40 are provided with individual insulating sleeve members 42. The electrical leads 36, 38 are shown being provided with a further insulating sleeve 44. Insulating sleeve members 42, 44 with their interiorly received electrical leads 34, 36, 38 and 40 are threaded through longitudinally extending bores or passages within, and which extend completely through, ceramic insulator member 16 from the bottom of well or cavity 22 to the rear face of ceramic insulator member 16. Electrical lead 34 and its associated insulating sleeve 42 are inserted into the insert portion 28a of electrical terminal member 28. The electrical lead 34 is electrically united with the electrical contact portion 28b of terminal member 28. Similarly, electrical lead 40 and its associated insulator member 42 are inserted into the insert portion 30a of second electrical terminal member 30. The electrical lead 40 is electrically united with electrical contact portion 30b of terminal member 30. The conductor formed by sensor leads 36, 38 and the associated insulator sleeve member 44 are similarly inserted into the insert portion 32a of electrical terminal 32 and the conductive portion thereof is electrically united with the electrical contact portion 32b of terminal member 32.

The ceramic sensor elements 24, 26 are situated within the well or cavity 22 and are shown to be supported by their associated electrical leads 34, 36, 38 and 40. Projecting collar 20 thus may be operative upon insertion of the exhaust gas sensor 10 into an exhaust gas system to shield the ceramic sensor elements 24, 26 from impact by any solid particles which may be dislodged from the interior surface of the exhaust gas conduit. Collar 20 also protects the electrical leads 34, 36, 38, 40 from flexure induced by pressure and exhaust gas flow fluctuations within the exhaust gas system. Collar 20 further protects the ceramic sensor elements 24, 26 and their electrical leads 34, 36, 38 and 40 from possible damage during assembly and from handling damage prior to or during installation into an exhaust gas system.

Ceramic insulator member 16 is provided with a centrally position enlarged annular portion 46 which is provided with a seal receiving recess 48 at its forward shoulder. Enlarged annular portion 46 is provided with an abutment shoulder 50 at its rear. The forwardly projecting portion 18 of ceramic insulator member 16 is inserted through seal member 52 and seal member 52 is loosely received within recess 48. The ceramic insulator member 16 is then inserted into housing means 12. The rear portion 54 of housing means 12 is then crimped or otherwise deformed into close intimate contact with the rear shoulder 50 of the central portion 46 of ceramic insulator means 16 to compressively and sealingly confine seal member 52 between recess 48 and a suitably provided shoulder within the central portion of housing means 12. Seal member 52 is operative to define a fluid tight barrier to flow around insulator member 16 through housing means 12. Seal member 52 is operative to establish a fluid tight barrier between the interior of an exhaust gas conduit and the exterior of the exhaust gas conduit into which an exhaust gas sensor 10 has been inserted.

Referring now to FIG. 3, the electrical series connection between ceramic sensor elements 24 and 26 and electrical leads 34, 36, 38 and 40 is illustrated. Electrical leads 36, 38 are electrically united, as by welding, at junction 56. A single electrical lead 37 extends from junction 56. With reference to FIGS. 1 and 2, electrical lead 34 communicates, for example, with terminal member 28, electrical lead 40 communicates, for example, with terminal member 30 and electrical lead 37 may extend through insulating member 44 to communicate sensor leads 36, 38 for example, with terminal member 32.

One of the ceramic sensor elements, for example sensor element 24, is a high temperature thermistor fabricated according to the present invention. The other of the sensor elements, for example sensor element 26, is a variably resistive partial pressure of oxygen responsive ceramic, such as for example titania, which also demonstrates an electrical resistance variation in response to changes in its temperature. The partial pressure of oxygen responsive sensor element 26 may be formed of titania material in the manner described in issued U.S. Pat. No. 3,886,785, titled, Gas Sensor and Method of Manufacture, issued in the name of Henry L. Stadler et al. and assigned to the assignee of this invention. The preferred form of partial pressure of oxygen responsive ceramic sensor element 26 to be used in fabricating exhaust gas sensor 10 is the improved formed described in the above noted copending commonly assigned, patent application Ser. No. 839,704, now U.S. Pat. No. 4,151,503, issued Apr. 24, 1979. Preferably, the thermistor member 24 and the partial pressure of oxygen responsive member 26 are fabricated from the same metal oxide ceramic forming base material. The advantage of this feature is discussed hereinbelow.

The thermistor ceramic sensor element 24 according to the instant invention is formed from essentially pure titania powder. The thermistor chip member 24 may be fabricated in much the same manner as is taught in the noted U.S. Pat. No. 3,886,785 to Stadler et al. for fabrication of partial pressure of oxygen responsive ceramic sensor elements with one principal difference. Where the fabrication of a partial pressure of oxygen responsive ceramic element must assure a level of porosity in order to achieve a suitably rapid response time for the device to be of utility as an air/fuel ratio feedback sensor, fabrication of a similar device which is intended to be responsive principally to variation in temperature necessitates processing to minimize responsiveness to variation in partial pressure of oxygen. We have determined that such a device may be achieved by processing the base powder material to produce a device having a density which approaches, as closely as possible, the theoretical density of the ceramic material. Thus, the one principal difference in processing is that the titania powder is processed to achieve a ceramic material density approaching, as closely as possible, the theoretical density of the material.

Densification of the titania ceramic material may be accomplished by several methods including high temperature sintering (that is, sintering at temperatures in excess of about 2700° F.) and/or through use of a titania powder having a particle size range adjusted for maximum densification during sintering. Since it is desirable to obtain substantially identical electrical response to temperature variation from the thermistor, element 24, and from the partial pressure of oxygen sensor, element 26, substantially the same titania powder material is used to form both ceramic sensor elements 24, 26. Since uniformity of particle size consonant with obtaining the desired ceramic porosity is beneficial to produce a satisfactory partial pressure of oxygen responsive sensor, element 26, we have relied upon high temperature sintering to achieve the desired densification of the thermistor sensor according to the present invention, element 24. While tests have indicated that even densified titania will continue to demonstrate some slight resistance variation as a function of partial pressure of oxygen, it also has been determined that the time rate of response of resistance changes to changes in partial pressure of oxygen increases dramatically with increasing density of the titania ceramic material. Increases in response time on the order of 10,000 times have been observed. The time rate of response for densified titania increases sufficiently that, for all practicel purposes in an internal combustion engine exhaust gas environment, the dependency of the thermistor resistance changes on partial pressure of oxygen changes can be ignored.

The preferred method of fabricating the thermistor chip member involves the preparation of a substantially pure titania powder. As titania has two phases, the anatase phase and the rutile phase, and the rutile phase is the high temperature stable phase, the titania powder could be comprised of a substantial majority of rutile phase material. In order to convert anatase phase material to rutile phase material, the material may be calcined, for example for two hours at 2100° F., and then ball milled to produce powder having small particle sizes. The majority of the powder so produced will be rutile phase material. Calcining also improves the purity of the powder by volatilizing any volitilizable impurties. Consonant with processing to achieve a partial pressure of oxygen responsive device, powder may have 100% of the particles smaller in size than 20 microns and may have a substantial majority of the powder with the particle size smaller than about 10 microns. The processed powders may thereafter be mixed, for example in a ball mill, with an organic binder solution to form a slurry.

The slurry may be cast, that is, formed onto a tape or sheet of material such as cellulose acetate or polytetrafluoroethylene (PTFE) after which the slurry may be air dried, to form a sheet or tape of material. Suitably sized and shaped sensor element wafers of the air dried material may then be cut from the tape for further processing. A pair of lead wires may be inserted into the sensor element at this stage and the sensor element may thereafter be sintered. In one form of construction, a pair of lead wires are placed between a pair of sensor element wafers prior to sintering. In another form of construction, a pair of lead wires are impressed into a single wafer prior to sintering. In order to achieve the desired high density titania thermistor, the step of sintering is carried out at a temperature of about 2750° F. for a period of one (1) hour. Sintering to a pyrometric cone equivalent number 18 or greater will achieve sufficient densification for starting powders which are not optimized for densification. If the powder particle size range is adjusted for densification, a lower pyrometric cone equivalent could be used. In no case should the sintering temperature cause liquification of the material.

It will be appreciated that the instant invention accomplishes its stated objectives. By using substantially identical starting materials and by adjusting the processing to yield a densified sensor chip member, the electrical response of the sensor chip members to temperature variation will be substantially identical while the responsiveness of the densified chip member to variation in oxygen partial pressure will be greatly reduced. The resulting ceramic thermistor is thus compatible with and suited for operational use with the titania partial pressure of oxygen responsive chip member.

I claim:

1. The method of manufacture of a thermistor operable at temperatures in excess of about 700° F. comprising the steps of forming a powder of high temperature stable phase ceramic forming metal oxide;
preparing sinterable wafers from said powder;
affixing electrodes to said wafers; and
sintering said wafers to achieve a ceramic body having a density greater than about ninety-seven percent (97%) of theoretical density.

2. The method of manufacture according to claim 1 wherein the step of sintering is carried out at a pyrometric cone equivalent number of at least eighteen (18).

3. The method of manufacture according to claim 1 including the step of forming the powder having a particle size range and distribution adjusted to achieve maximum densification.

4. The method of manufacture according to claim 3 wherein the step of sintering is carried out at a temperature in excess of about 2700° F.

* * * * *